(12) United States Patent
Waldhauser et al.

(10) Patent No.: US 6,939,338 B2
(45) Date of Patent: Sep. 6, 2005

(54) METHODS AND APPARATUS FOR IMPARTING CURVES IN ELONGATED MEDICAL CATHETERS

(75) Inventors: Steven L. Waldhauser, Circle Pines, MN (US); Timothy G. Laske, Shoreview, MN (US); James F. Kelley, Coon Rapids, MN (US); Kenneth C. Gardeski, Plymouth, MN (US); Gregory P. Shipe, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 364 days.

(21) Appl. No.: 10/125,365

(22) Filed: Apr. 19, 2002

(65) Prior Publication Data

US 2003/0199818 A1 Oct. 23, 2003

(51) Int. Cl.[7] .............................................. A61M 25/00
(52) U.S. Cl. ...................................... 604/531; 604/528
(58) Field of Search .......................... 604/95.05, 95.01, 604/531, 523, 500, 508, 528

(56) References Cited

U.S. PATENT DOCUMENTS

| | | | |
|---|---|---|---|
| 3,890,977 A | 6/1975 | Wilson | 128/418 |
| 4,799,474 A | 1/1989 | Ueda | 128/4 |
| 4,918,919 A | 4/1990 | McCoy et al. | 60/528 |
| 4,919,133 A | 4/1990 | Chiang | 606/159 |
| 5,055,101 A | 10/1991 | McCoy | 604/95 |
| 5,201,901 A | 4/1993 | Harada et al. | 606/198 |
| 5,279,559 A * | 1/1994 | Barr | 604/95.05 |
| 6,072,154 A | 6/2000 | Maynard | 219/209 |
| 6,133,547 A | 10/2000 | Maynard | 219/209 |
| 6,278,084 B1 | 8/2001 | Maynard | 219/209 |
| 6,306,141 B1 | 10/2001 | Jervis | 606/78 |

OTHER PUBLICATIONS

Takizawa, "Development of a Microfine Active Bending Catheter Equipped with MIF Tactile Sensors", IEEE, 1999.

* cited by examiner

Primary Examiner—Kevin C. Sirmons
(74) Attorney, Agent, or Firm—Girma Wolde-Michael; Michael C. Soldner (57) ABSTRACT

Curves and dynamic shapes are imparted in distal segments of medical instruments e.g., catheters, through use of a temperature-activated actuator coupled to distal segment of the instrument body. The actuator comprises includes members extending side-by-side in substantially a common plane and configured to move in opposite directions when independently activated. A first heating device is coupled to a first actuator member and configured to deliver thermal energy to the first actuator member to activate the first actuator member and cause the first actuator member to move the distal segment in a first direction. A second heating device is coupled to a second actuator member and configured to deliver thermal energy to the second actuator member to activate the second actuator member and cause the second actuator member to move the distal segment in a second direction opposed to the first direction.

19 Claims, 5 Drawing Sheets

METHODS AND APPARATUS FOR IMPARTING CURVES IN ELONGATED MEDICAL CATHETERS

FIELD OF THE INVENTION

The present invention pertains to elongated medical instruments, e.g., catheters, adapted to be temporarily inserted into the body to access a site in the body, and particularly to methods and apparatus for deflecting the distal end and imparting curves in distal segments of such medical instruments for directed navigation within the body by manipulation of a proximal mechanism of the instrument outside the body.

BACKGROUND OF THE INVENTION

A wide variety of elongated medical instruments that are adapted to be permanently or temporarily implanted in the mammalian body, usually the body of a human patient, or used to access a site in the body to facilitate introduction of a further medical device. Such elongated medical instruments have an instrument body extending between instrument body proximal and distal ends, and a distal segment of the instrument body is advanced to a remote site in the body by manipulation of a proximal segment of the instrument body or a handle or stylet or the like extending from the instrument body proximal end located outside the body.

Elongated medical instruments include implantable medical electrical leads, catheters, sheaths, endoscopes, guidewires, and the like. In the case of a medical electrical lead, the lead body proximal end is coupled to an implantable pulse generator (IPG) of an implantable cardioverter/defibrillator (ICD) or pacemaker or to a monitor that is then implanted subcutaneously or to an external medical device located outside the body and electrical signals are conducted to or from the remote site in the body through one or more lead conductors. Catheters typically extend through the patient's skin and are coupled with external diagnostic or therapeutic equipment or are used to introduce other elongated medical instruments or fluids or cells or proteins or the like, or to withdraw fluids or measure pressure, or the like, through a catheter lumen open at the accessed remote site. Certain catheters, e.g., electrophysiology ablation and mapping catheters, also deliver electrical energy or conduct electrical signals of the body. Other catheters include pulmonary artery catheters, central venous catheters, diagnostic coronary catheters, intra-aortic balloon pump catheters, balloon tipped (PTCA)/angioplasty catheters, and stent delivery catheters. The terms "catheter" and "lead" are often interchanged in these and other contexts. Guidewires are small diameter wires that are directed through tortuous pathways to provide for advancement of medical leads or catheters over-the-wire. Certain guidewires are also designed to function as a micro-catheter for infusion of fluids through a guidewire lumen. Other guidewires include insulated electrical conductors connected at the guidewire proximal end with an external medical device to deliver electrical energy for tissue stimulation or to conduct electrical signals of the body to the external medical device. Hence, in the following discussion, the terms electrical medical leads, catheters and guidewires comprise and can be used interchangeably with elongated medical instruments.

In many cases, the introduction of such elongated medical instruments to a remote site in the body is effected through a needle (Seldinger Technique) or skin incision accessing a blood vessel, whereby the instrument body is advanced through a vascular pathway until the distal segment or the instrument body distal end are located at the remote site. Such advancement is often through a tortuous pathway having twists and turns requiring the capability to impart a curve or deflect the instrument body distal end to facilitate advancement. Therefore, the introduction of such elongated medical instruments through vascular pathways or other tortuous pathways in the body is facilitated by a wide variety of techniques and mechanisms that have been developed to impart curves in the distal segment of the instrument body or to deflect the instrument body distal end.

One typical approach facilitating catheter introduction involves one or multiple needles, guide wires, dilators and hemostatic sheaths. The needle gains access to the vasculature (vein or artery), and a guidewire is inserted through the needle for pathway retention. The needle is removed. A dilator is inserted into a hemostatic sheath, which can then be advanced over the retaining guidewire and into the pathway. The guidewire and dilator are removed. The sheath can be advanced closer to target locations. A guidewire or guide catheter can be inserted into the hemostatic sheath for access retention or further steering functionality. In this case, a catheter lumen terminates in a distal lumen end opening allowing the catheter to be inserted over the proximal end of the guidewire outside the body. Another approach employed with closed end catheters and medical electrical leads involves preforming a curve into the distal end segment of a stiffening stylet and inserting the stylet into a catheter or lead lumen to curve or deflect the corresponding distal segment of the catheter or lead. The distal segments of certain stylets and guidewires can alternatively be deflected within the lumen by operating a shaping mechanism of the types described below at the proximal end of the stylet or guidewire outside the body.

One or more pull wire or push-pull wire mechanisms are commonly employed to provide controllable deflection of the distal end segments of catheters and guidewires. Typically, the catheter, or guidewire is formed having a generally straight outer sheath and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes a distal segment of the outer sheath controlled to bend or deflect. Various mechanisms are employed to control the direction of deflection of each segment.

In another approach, one or more piezoelectric member or shape memory material member, particularly a shape memory alloy (SMA) member, that bends from a first shape or direction to a second shape or direction upon application of electrical energy to the member is incorporated into a deflectable segment of a catheter, medical electrical lead or guidewire. The characteristics of SMA materials and particular examples of SMA members incorporated into catheter or guidewire bodies are described in the literature and in a number of patents including U.S. Pat. No. 3,890,977 to Wilson, U.S. Pat. No. 4,799,474 to Ueda, U.S. Pat. Nos. 4,918,919 and 5,055,101 to McCoy, U.S. Pat. No. 6,306,141 to Jervis, and U.S. Pat. Nos. 6,133,547 and 6,278,084 to Maynard. SMA members are also referred to as actuators or elements that are activated in certain of the above-referenced patents.

As described in the above-referenced '547 patent, SMA material undergoes a micro-structural transformation from a martensitic phase at a low temperature to an austenitic phase at a transition temperature. When in the martensitic or low temperature phase, SMA exhibits low stiffness (low elastic modulus) and may be readily deformed up to 8% total strain in any direction without adversely affecting its memory properties.

Upon being heated to its activation temperature, the SMA becomes two to three times stiffer as it approaches its austenitic state. The higher elastic modulus, at the higher temperature, is the result of the SMA reorganizing itself on the atomic level to a body-centered cubic (BCC) crystal structure to return to a previously imprinted or "memorized" shape, if unrestricted. Useful motions and forces may be extracted from a SMA element as it attempts to move to its previously memorized shape. If permitted to cool below the transformation temperature, the BCC crystal structure goes through a diffusionless shear transformation to a highly twinned martensite crystal structure. A shape may be "trained" into a SMA by heating it well beyond its activation temperature to its annealing temperature for a period of time. In one example for a TiNi (sometimes referred to as Nitinol) SMA system, the annealing program consists of geometrically constraining the specimen, and heating it to approximately 510° C. for fifteen minutes.

The point at which a SMA becomes activated is an intrinsic property of the material and is dependent on stochiometric composition. A change in alloy ratios of 1% produces a 200° C. shift in transition temperature, for a typical SMA such as TiNi (49:51). Binary TiNi SMAs can have a large range of transition temperatures. For Nitinol, atomic composition can be adjusted for a phase transition as high as 100° C. and as low as −20° C. or more. Sub-zero transition materials exhibit superelastic behavior. That is, they can reversibly endure very large strains at room temperature. In the medical community, superelastic formulations of Nitinol are commonly employed in "steerable" guidewires or catheters.

In contrast to the passive characteristics of a superelastic SMA, a SMA actuator that must perform work on its environment requires a SMA capable of producing useful forces and motions for a given input of thermal energy. Because most thermal devices must expel their waste heat to the ambient environment, which in most cases is near room or body temperature, higher transition point SMAs are most commonly used as active actuator elements. During phase changes, a SMA will exhibit a maximum recoverable strain of up to 8%. In general, electrical energy is applied to a SMA member or to a resistive heating element adjacent to the SMA member to cause the SMA member to heat up and bend in the second direction. The bend in the second direction is maintained until the energy is removed and the SMA member cools, whereupon it bends back toward the first direction. Such SMA members are also referred to as actuators or elements that are "activated" when heated by applied energy in certain of the above-referenced patents.

The SMA element is typically formed of an elongated strip of SMA element disposed to extend lengthwise along the catheter segment as disclosed in the above-referenced '977 patent. The catheter segment is bent to the second direction upon application of electrical current directly to the elongated SMA member to heat it. SMA materials do not fully return to the first shape or direction after cooling, and other mechanisms (externally applied forces) are required to restore the first shape or direction. The restoration can be accomplished actively or passively through further components incorporated into the segment of the catheter. For example, a return spring can be incorporated into the segment that is just strong enough to fully deflect the SMA member in the first direction in its (cool) martensitic state. The SMA member exerts enough force when activated to overcome the passive return spring force and bend or deflect the segment of the catheter in the second direction. The passive return spring force bends or deflects the segment back in the first direction when the SMA member is de-activated. Thus, the forces work in opposition to one another in the plane of the induced bend.

In an active or antagonistic configuration as disclosed in certain embodiments of the above-referenced '101 and '474 patents, first and second elongated SMA elements or members are captured by a common catheter segment that is to be deflected. The first and second elongated SMA members are captured by the catheter sidewall such that they extend in parallel with one another and the catheter axis and are displaced 180° apart around the sidewall, that is, diametrically across the catheter diameter. When the first SMA member is heated to its activation temperature, it provides sufficient force to deflect itself, the second SMA member, and the catheter sidewall segment in the first direction. When the second SMA member is heated to its activation temperature, it provides sufficient force to deflect itself, the first SMA member, and the catheter sidewall segment in the second direction. Again, the forces are diametrically opposed or antagonistic to one another such that the activated SMA member must apply force to bend the inactivated (martensitic or soft) SMA member from its proximal end or root disposed diametrically across the diameter of the catheter shaft as well as the catheter sidewall itself.

In the above-referenced '474 and '919 patents, the electrical current is applied directly through conductors attached at opposite electrical ends of the SMA member. The SMA member is formed as either an elongated bar of SMA material, so that the opposite electrical connection ends are located at different distances along the length of the catheter shaft, or a U-shaped split bar of SMA material, so that the opposite electrical connection ends are located at a common point along the length of the catheter shaft. As noted in the '919 patent, the attachment of electrical conductors to the opposite ends of the SMA member contaminates the SMA alloy and negatively affects performance, and steps are disclosed for isolating the contamination areas. In either case, the applied electrical current directly heats the SMA member that responds by bending along its length in the non-contaminated area by an amount that depends on composition, dimensions, and heat treatment of the SMA member.

In the '084 patent, various embodiments of a SMA actuator are disclosed comprising a SMA member that is electrically insulated from a plurality of resistive heating elements deposited or formed overlying and in close proximity to the SMA member. The SMA member is preferably formed as a two-dimensional strip or sheet of SMA material that can bend in one or two dimensions. Directing electrical current to selected resistive heating elements overlying the discrete portions effects the bending of discrete portions of the SMA member. A flexible layer of insulation is deposited over the SMA strip or sheet, and the resistive heating elements and conductive traces from bond pads to the resistive heating elements are formed on the electrically insulating layer. In this way, direct electrical connection with and application of current to the SMA material is avoided, and discrete portions of the SMA material can be activated. Moreover, micro-machining and integrated circuit fabrication techniques can be employed to form SMA actuators in a wide array of configurations.

In one disclosed configuration, a tubular SMA actuator is formed as described above and mounted along the shaft of a catheter or a guidewire or the like. Longitudinally extending, parallel slits are formed in the tubular SMA actuator, thereby providing a plurality of longitudinally extending "finger-like segments" extending from a common cylindrical band encircling the catheter shaft. Each finger-like segment comprises at least one or a plurality of resistive heating elements and conductive traces deposited as described above. Thus, each finger-like segment comprises discrete portions of SMA material that are selectively bendable, whereby the entire finger-like segment is bendable to a selective degree depending upon selective current flow through the discrete resistive heating elements. This system could work in theory, but practically would be difficult to reduce to practice.

U.S. Pat. No. 6,072,154 (FIGS. 24A–24C) depicts incorporation of the tubular SMA actuator into a catheter shaft and selectively activating the finger-like segment along one side as described above to enable selective bending of the catheter shaft as the finger-like segment bends outward and pulls the inactivated finger-like segments along in the direction of the bend. Presumably, the catheter shaft could be bent in any direction away from the shaft axis through selective activation of any of the finger-like segments arrayed through 360° about the axis. But, the activation energy required to actuate any one or more finger-like segment and pull along the remaining inactivated finger-like segments disposed around the catheter shaft would appear to be high. The resistance of multiple inactive finger-like segments would make it difficult to bend the catheter shaft by activating any of the finger-like segments.

While the mechanisms disclosed in the above cited prior art patents may at least to some degree be workable, there is still a need for a SMA deflection mechanism that is simple, inexpensive to manufacture, does not excessively increase the elongated medical instrument body diameter, and reduces the bending forces and stress/strain that are necessary to deflect the distal segment of the catheter body while enhancing the control of the deflection and the imparted curvature of a catheter body distal segment.

SUMMARY OF THE INVENTION

Accordingly, in the present invention, SMA actuators are incorporated into elongated medical instruments to effect selective deflection of an instrument distal segment in generally opposed first and second directions wherein the flexural stiffness that the SMA actuators work against is reduced.

In accordance with the present invention an elongated medical instrument is provided and operated advantageously that has an elongated instrument body having a proximal segment and a distal segment. A temperature-activated SMA actuator is coupled to the distal segment of the elongated instrument body, the actuator comprising at least two elongated actuator members or SMA actuator members. The actuator members are individually activated to perform work by moving, bending or deflecting the distal segment, including the inactivated actuator member in respective first and second directions out of straight axial alignment with the proximal segment.

In one aspect of the invention, the first and second directions are opposed to one another, and one of the actuator members is more robust than the other actuator member and is used as the primary actuator member to form bends in or deflect the distal segment by a desired amount. The other, less robust, actuator member is relatively easier to deflect so that work performed by the more robust actuator member is lessened. The less robust actuator is activated to move the distal segment back into substantially axial alignment with the proximal segment.

In a second aspect of the invention, the first and second actuator members extend side-by-side in substantially a common plane and are each configured to move in opposite first and second directions when independently activated. Thus, the first and second actuator members do not directly bend against one another when activated.

In a further aspect of the invention, the first and second actuator members are mounted in or on or otherwise supported by the instrument sidewall of the distal segment to extend side-by-side in substantially a common plane so that they move in opposite first and second directions when independently activated. Advantageously, the side-by-side relationship of the first and second elongated actuator members in substantially a common plane reduces flexural stiffness in the first and second direction, and provides a simpler form of fabrication than is the case in the above-described prior art patents.

The first and second elongated actuator members preferably extend from a fixed end to a free end, are substantially the same in length. When a bend is induced by energizing or heating one of the first and second elongated actuator members, the other elongated actuator member bends along with and to the same degree as the energized or heated elongated actuator member. Since both of the first and second actuator members are on the same side of instrument sidewall the shearing stresses that occur when they are on opposite sides of displaced around the sidewall are avoided.

The first and second actuator members are preferably each formed of SMA material or a layer of SMA material that is selectively heated either directly or indirectly. A first heating device is coupled to the first elongated actuator member and configured to deliver thermal energy to the first elongated actuator member to activate the first elongated actuator member and cause the first elongated actuator member to move the distal segment in a first direction. A second heating device is coupled to the second elongated actuator member and configured to deliver thermal energy to the second elongated actuator member to activate the second elongated actuator member and cause the second elongated actuator member to move the distal segment in a second direction opposed to the first direction.

In a further embodiment of the invention, the first and second heating devices comprise first and second pluralities of heating elements in respective first and second heating element arrays along the lengths of the first and second actuator members. The heating elements are sized and spatially displaced apart from one another and disposed in operative relation to respective spatially displaced portions of the SMA material of the first and second segment. One or more or all of the individual heating elements are energized to selectively indirectly heat one or more or all of the respective portions of the SMA material and induce a deflection of the actuator member free end that is proportional to the number of the heated portions and the spatial relation of the heated portions.

In this embodiment of the invention, one of the first and second elongated actuator members can advantageously be formed more robustly than the other of the first and second elongated actuators to operate as a power actuator member that moves or bends the distal segment through a wide range of motion by making it physically larger and having a greater number of heating elements. The other of the first and second elongated actuator members can advantageously be formed less robustly by making it narrower and with fewer and differently shaped heating elements. In this way, the less robust elongated actuator member can be more easily moved or bent by the power actuator member and can be used to simply restore the distal segment into axial alignment with the proximal segment to remove a bend in the distal segment formed by the power actuator member.

The above-described aspects of the invention may be advantageously employed separately or in combinations.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. The preferred embodiments of the invention are described in relation to endocardial cardiac leads, particularly endocardial pacing and/or cardioversion/defibrillation leads, but it will be understood that the present invention can be utilized in any elongated medical catheters of the types described or mentioned herein and equivalents that may presently exist or come into existence in the future.

Figure 1:
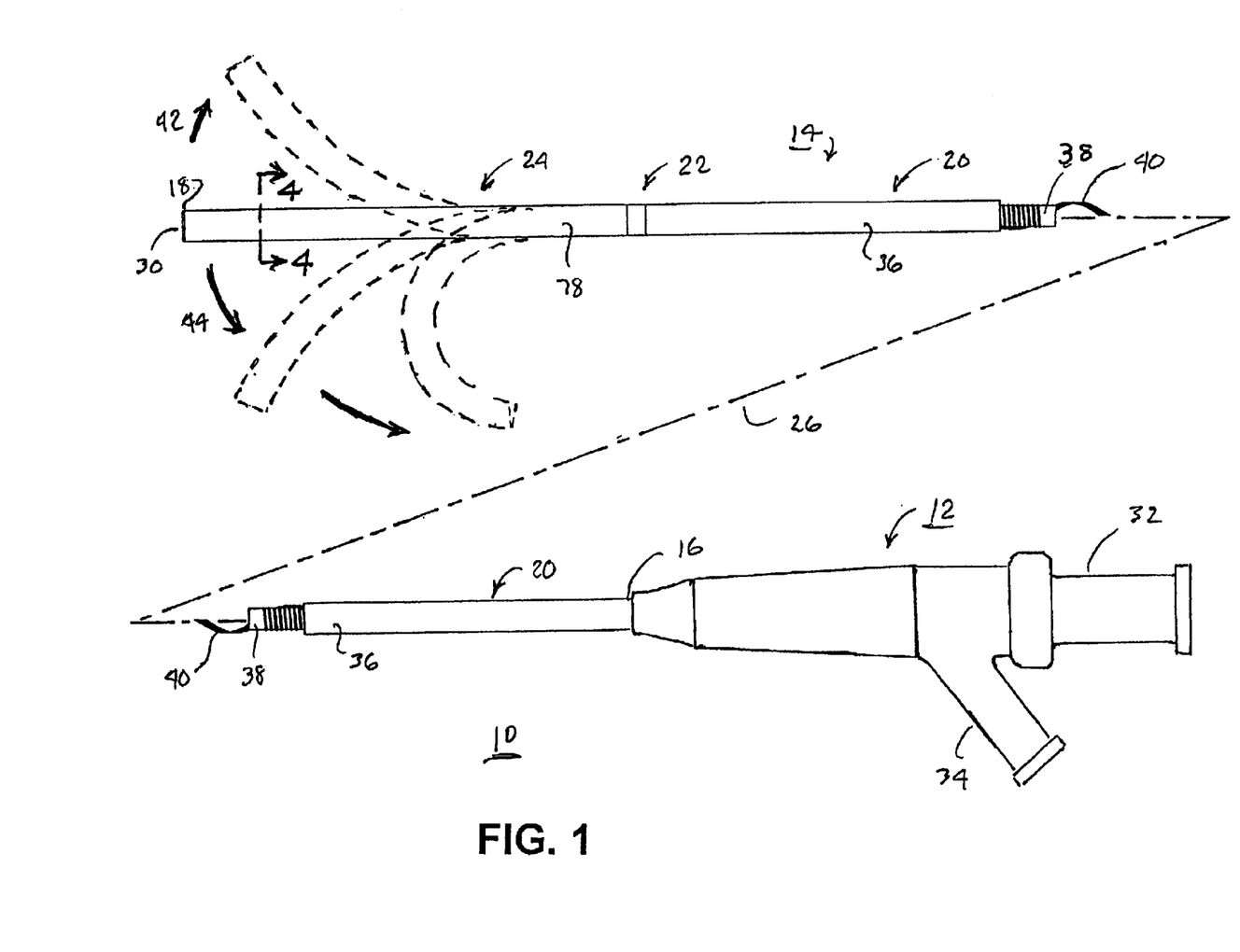
FIG. 1 is a plan view of an exemplary elongated medical instrument of the present invention, in this case a catheter, having a deflectable distal segment.

FIG. 1 illustrates an exemplary elongated medical instrument of the present invention, e.g., a catheter 10 formed of a proximal connector 12 and a catheter body 14 extending between a catheter body proximal end 16 and a catheter body distal end 18. The catheter body 14 is formed of a relatively straight proximal segment 20 joined at an intermediate junction 22 with a deflectable distal segment 24 that is fabricated and operates as described below.

A catheter lumen 30 extends from the proximal connector 12 through the length of the catheter body 14 in axial alignment with or parallel to the catheter body axis 26 and terminates in a distal end opening at catheter body distal end 18. The proximal connector 12 is formed of an axially aligned main branch 32 and a side branch 34. The catheter lumen 30 can be accessed through the main branch in a manner well known in the art. The side branch 34 comprises an electrical connector for making electrical connection between conductors extending through the catheter body proximal segment 20 to the SMA actuator in the catheter body distal segment 24 and an external console that is operated by medical personnel to selectively provides electrical energy to the SMA actuator to cause it to deflect the distal segment 24 in a manner described below.

The sidewall of the catheter body proximal segment 20 can be formed in any of the manners known in the art. The catheter body proximal segment 20 is preferably formed of an outer jacket 36 of Atofina Chemicals, Inc. PEBAX® polymer resin that may be reinforced with polymer or metal wire braid or a coiled metal or polymer wire in a manner well known in the art. The outer jacket 36 surrounds an inner sleeve or liner 38 of PTFE that in turn surrounds and defines the catheter lumen 30. A flat multi-conductor ribbon wire or flex-tape 40 is helically wound about the liner 38 and interposed between the outer jacket 36 and the inner liner 38. The flat ribbon wire or flex-tape 40 is formed of two or more conductors arranged side-by-side that are embedded within a polyimide layer and thereby insulated from one another.

Figure 2:
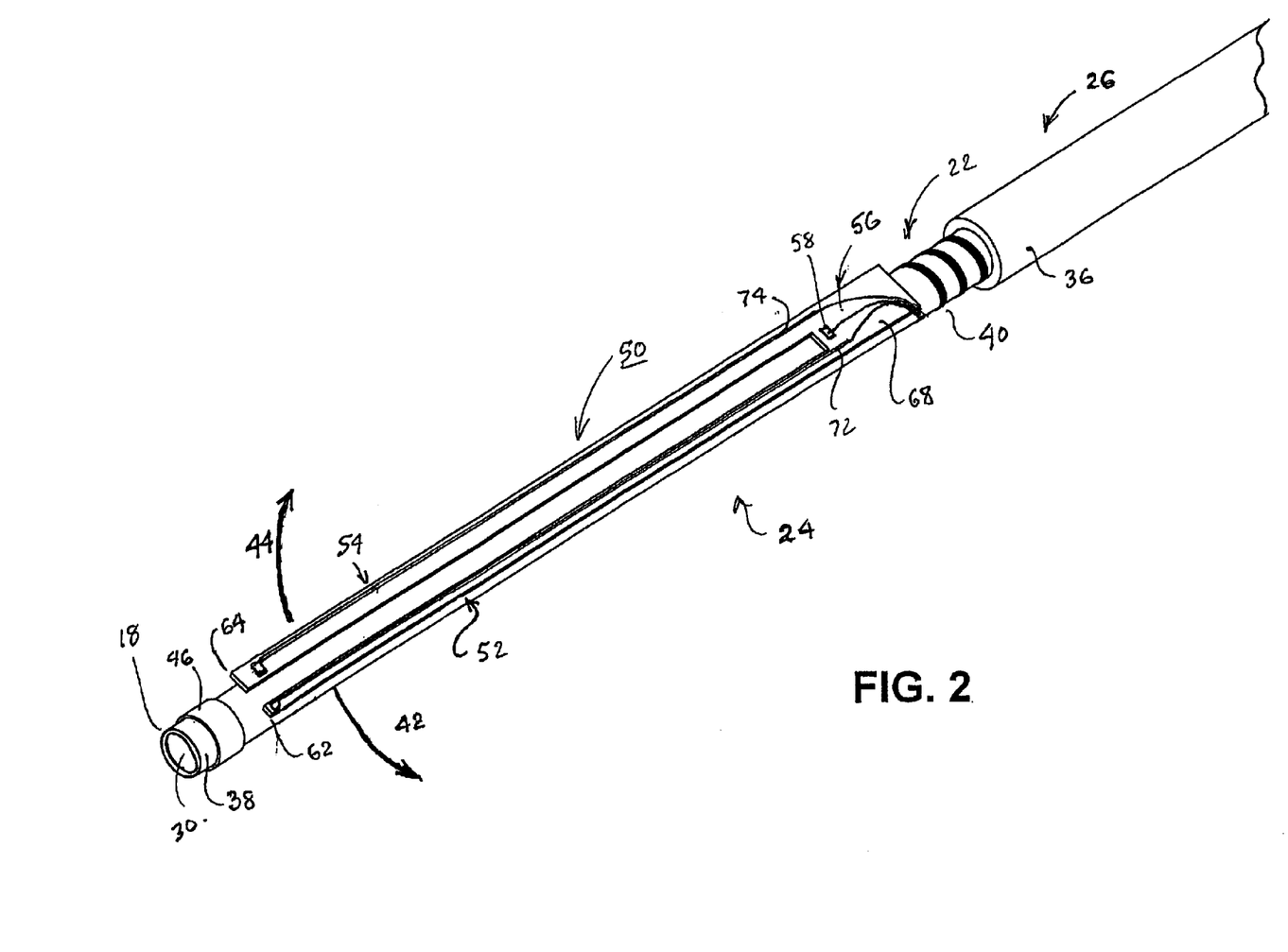
FIG. 2 is a simplified schematic view of the relationship of the temperature-activated actuator to the deflectable distal segment of the catheter body of FIG. 1.

The distal segment 24 is formed differently in ways depicted in FIGS. 2–5 and described further below. In accordance with the present invention, the temperature-activated actuator 50 is coupled to the distal segment 24 of the elongated instrument body 14 as schematically depicted in FIG. 2. As described further below, the actuator 50 preferably comprises first and second elongated actuator members 52 and 54 extending substantially side-by-side in substantially a common plane. When independently activated, the first and second elongated actuator members 52 and 54 are configured to move in opposite directions 42 and 44, respectively, in a common bending plane. The first and second elongated actuator members 52 and 54 extend substantially parallel to the instrument body axis along one side and within or attached to the sidewall of the distal segment 24 and substantially in a common plane. In one embodiment, actuator 50 comprises a sheet or layer of SMA material that is cut into the depicted U-shape including the first and second elongated actuator members 52 and 54 joined together at a fixed actuator end 56 and extending distally to first and second respective distal free ends 62 and 64, respectively.

The first elongated actuator member 52 is formed of a layer of SMA material that retains an elevated temperature shape memory that induces a deflection of a first actuator member free end 62 in the first direction 42 when heated to a transition temperature. Similarly, the second elongated actuator member 54 is formed of a layer of SMA material that retains an elevated temperature shape memory that induces a deflection of the second actuator member free end 64 in the second direction 44 when heated to a transition temperature.

The shape memory training can be accomplished in a variety of ways. In one approach, a fixture with pins was produced to hold the U-shaped SMA in an appropriate shape. Elongated actuator member 52 was held by a series of pin pairs along a relatively large radius (0.75"–1.0", as an example), and elongated actuator member 54 was held by another series of pin pairs along a relatively small radius (<0.5"). The fixture was then placed in a vacuum oven, heated beyond 500° F. for ~15 minutes, cooled to room temperature, and removed from the fixture. The resulting elongated actuator members 52 and 54 are soft and can be bent easily at room and body temperature. The actuator members 52 and 54 bend to their trained (annealed) state by heating the selected actuator member 52 or 54 to and beyond the activation temperature.

One of the first and second elongated actuator members 52 and 54 can advantageously be formed more robustly than the other of the first and second elongated actuators 52 and 54 to operate as a power actuator member that moves or bends the distal segment through a wide range of motion. The other of the first and second elongated actuator members 52 and 54 can advantageously be formed less robustly so that it can be more easily moved or bent by the power actuator member and can be used to simply restore the distal segment 24 into axial alignment with the proximal segment 26 to remove a bend in the distal segment formed by the power actuator member.

Thus, the degree of movement or bending of the distal segment 24 in the direction 44 is preferably greater than the degree of movement or bending of the distal segment 24 in the direction 42 as shown in the broken line positions depicted in FIG. 1. It is preferable that the distal segment 24 be capable of being deflected or bent in direction 44 into a 90° or 180° or greater bend as shown in broken lines in FIG. 1. The distal segment 24 may not fully return to the straight alignment with the proximal segment 26 depicted in full lines in FIG. 1 after the distal segment 24 is bent in direction 42 or 44 upon heating and subsequent cooling of the first or second actuator member 52 or 54, respectively, due to the nature of the polymer materials used to fabricate the distal segment and the actuator members themselves. Consequently, it may be necessary to heat the other of the first or second actuator member 52 or 54 to induce a bend in the opposite direction to restore the straight alignment.

When either the first or second elongated actuator member 52 or 54 is activated and bends or deflects, it develops a force sufficient to bend or deflect the other inactivated one of the first or second elongated actuator member 52 or 54 along with it. The force required to move, bend or deflect the inactivated one of the first or second elongated actuator member 52 or 54 is lesser than would be the case if the first and second actuator members 52 and 54 were not substantially coplanar on the same side of the catheter body sidewall.

In a further aspect of the present invention, the first elongated actuator member 52 is made narrower and less robust than the second elongated actuator member 54. The flexural stiffness of the first actuator member 52 is therefore less than the flexural stiffness of the second actuator member 54. The primary function of the more robust second elongated actuator member 54 is to deflect or form the bends depicted in FIG. 1 in the direction 44, and that function is made easier by making the first elongated actuator member 52 narrower than the second elongated actuator member 54. The primary function of the less robust first elongated actuator member is to restore the straight alignment of the distal segment 24 with the proximal segment 26 and that minor degree of movement in direction 42 can be effected with the narrower first elongated actuator member 52.

A first heating device is coupled to the first elongated actuator member 52 and configured to deliver thermal energy to the first elongated actuator member 52 to activate the first elongated actuator member 52 and cause it to apply force against and move the distal segment 24 in the first direction 42. A second heating device is coupled to the second elongated actuator member 54 and configured to deliver thermal energy to the second elongated actuator member 54 to activate the second elongated actuator member 54 and cause it to apply force against and move the distal segment 24 in the second direction 44 opposed to the first direction 42.

In one embodiment, first and second heating devices selectively, but directly heat the first and second elongated actuator elements by applying current directly through them thus, FIG. 2 shows that the first and second heating devices can comprise pairs of wires of the flat ribbon wire or flex-tape 40 attached directly to the first and second elongated actuator members to selectively directly heat the first and second elongated actuator members, respectively. Electrical current is selectively applied from the external power supply to specific conductors of flex-tape 40 through terminal pins of the connector 34 to effect the selective bending of the first or the second actuator to induce movement or bending of the distal segment 24 in the directions 42 and 44, respectively.

In this embodiment schematically depicted in FIG. 2, an insulation layer of polymer is formed over the upper surface of the electrically conductive SMA material. Conductive traces 72 and 74 are deposited on or adhered to the insulated upper surface that extend to the distal free ends 62 and 64, respectively, where they are electrically connected by vias through the insulation layer to the SMA material as shown in FIG. 2. A further ground trace 58 is formed over the insulation on the proximal fixed end 56 and a via formed extending through the insulation layer to the SMA layer. Individual wires from the flex-tape 40 are electrically coupled to the conductive traces 58, 72 and 74. Thus, electrical current can be selectively applied through traces 72 and 58 directly to the first elongated actuator member 52 or through traces 74 and 58 directly to the first elongated actuator member 54.

In a variation of the direct heating embodiment, the first and second elongated actuator members 52 and 54 are each formed of round wire bent into an elongated U-shape or a rectangular sheet or layer cut into or wire bent into a U-shape. Each such actuator member 52, 54 would have first and second proximal ends and a U-turn or connection at the distal free end. The second proximal end of each such actuator element would be coupled in common to a return or ground trace 58 coupled to a conductor of the flex wire 40. Each first proximal end would each be coupled to a separate conductor of flex wire 40 so that electrical current can be selectively directed through each of the first and second elongated actuator members 52 and 54. The traces 72 and 58 would then be unnecessary, but it would be necessary to mount each first and second proximal end to an insulating substrate at the proximal mounting in substitution for proximal fixed end 56. The overall shape of this variation would appear as shown in FIG. 2.

In a further embodiment, first and second heating devices selectively, but indirectly heat the first and second elongated actuator elements in their entirety or in selected portions displaced along the first and second elongated actuator members 52 and 54. Preferably, the first and second heating devices comprise groups of wires of the flat wire flex-tape 40 that are attached to individual heating elements displaced along the first and second elongated actuator members 52 and 54, respectively, for selectively heating discrete spatially displaced portions of the first and second elongated actuator members 52 and 54, respectively. Electrical current is selectively applied from the external power supply to specific conductors of flex-tape 40 through terminal pins of the connector 34 to effect the selective bending of the first actuator member in direction 42 or the second actuator member in direction 44. This embodiment of actuator 50' is depicted in greater detail in FIG. 5 and described further below.

Figure 3:
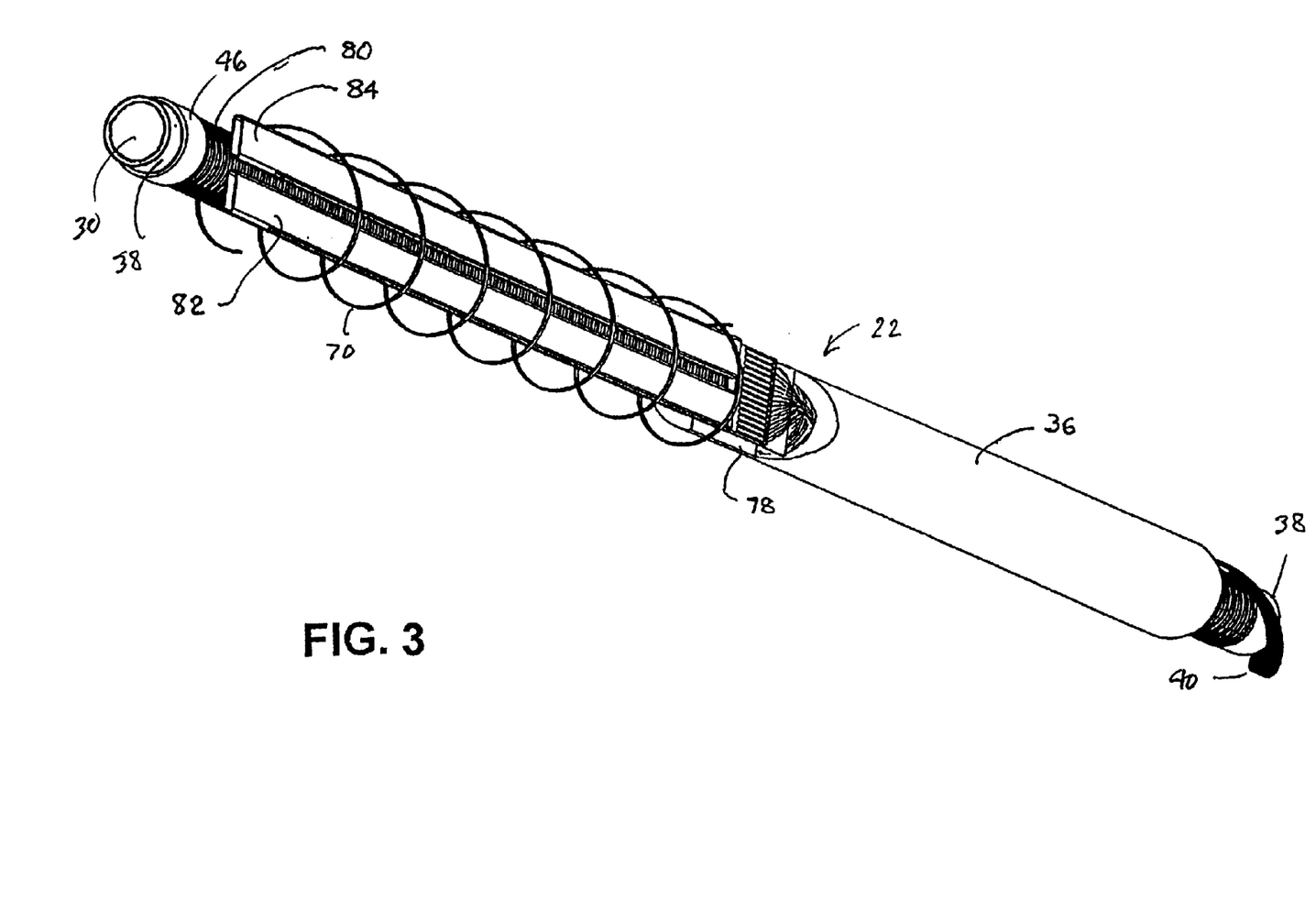
FIG. 3 is a perspective view of the distal segment of the catheter body without the outer insulation coating depicting the internal components thereof.
Figure 4:
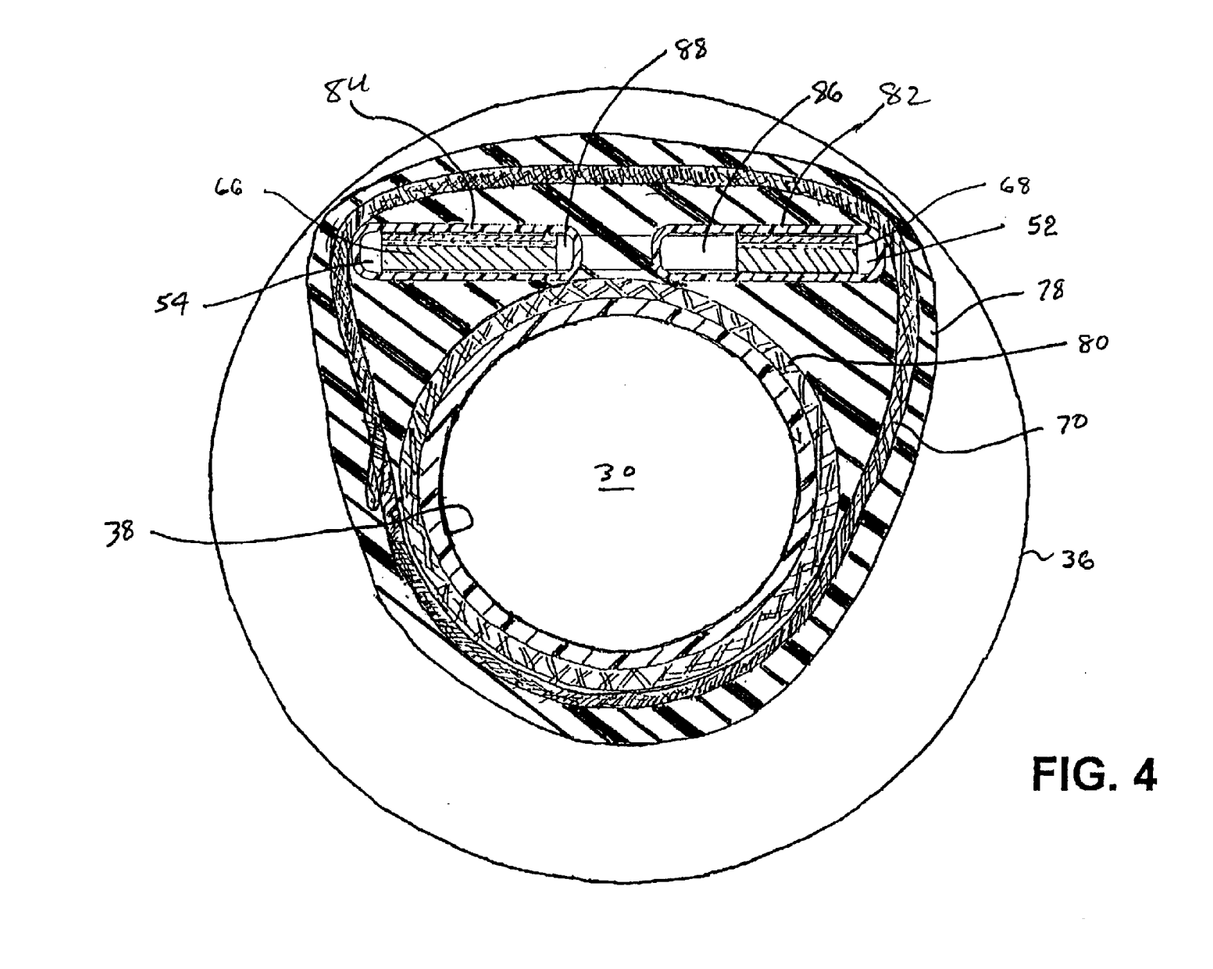
FIG. 4 is a cross-section view of the distal segment of the catheter body of FIG. 1 taken along lines 4—4.

First, however, common features to both embodiments that are not depicted in FIG. 2 to simplify the illustration of the principles of the invention are described in reference to FIGS. 3 and 4. The inner liner 38 is reinforced with a polymer or metal wire braid or a coiled metal or polymer wire reinforcement layer 80 over its outer surface to increase its hoop strength and inhibit collapse of the liner 38 when it is deflected or bent as depicted in FIG. 1. The inner liner 38 and reinforcement layer 80 can extend through the proximal segment 26. A radiopaque ring 46 is fitted about the distal end of the liner 38 to assist in guiding the distal tip during introduction using fluoroscopic imaging equipment.

The electrical attachments of the traces on the first and second elongated actuator members 52 and 54 with the wires flex-tape 40 are made in a bond pad area of the U-shaped fixed end 56. Loosely fitting, closed end, highly flexible sleeves 82 and 84 are fitted over the first and second elongated actuator members 52 and 54, respectively, so that the first and second elongated actuator members 52 and 54 are received in sleeve lumens 86 and 88, respectively. The SMA actuator 50 or 50' is maintained in place against the reinforcement layer 80 in the sidewall of the distal segment 24 by a loosely coiled filament or braid 70 that is wound about it and around the liner 38. The U-shaped fixed end 56 is supported on a shelf 78 formed in the distal end of the PEBAX® sheath 36, and the filament 70 is tightly wound around the U-shaped fixed end 56 over the bond pad electrical connections with the flex-tape 40. In this way, the U-shaped fixed end 56 is immobilized, the shelf 78 provides a strain relief at the junction 22, and to avoid a bulge in the catheter body diameter at the junction 22.

The distal end opening of the lumen 30 is plugged, and the assembly of the components of the distal segment 24 is then dip coated with a liquid silicone rubber-XYLENE compound that is then dried to form an outer sheath 78 of the distal segment 24. A silicone rubber compound is employed because it is very flexible and easy to bend and is less likely to thermo-set when exposed to heat generated in or applied to the SMA material of the actuator 50 than thermoplastic polymers. The resulting exterior end view of the distal segment sheath 78 shown in FIG. 4 is likely to be irregular but can be made the same or smaller in cross-section than the cylindrical outer sheath 36 of the proximal segment 26. The cross-section can be tapered somewhat from the junction 22 to the catheter body distal end 18. A uniform diameter of the distal segment 24 with the proximal segment 26 can be achieved by multiple dip coatings and shaping of the viscous silicone rubber-XYLENE compound before it dries, but a lesser thickness coating may suffice and advantageously decreases the bending resistance of the instrument body sidewall.

The silicone rubber dries as a mass over the first and second elongated sleeves 82 and 84 and immobilizes them. However, the silicone rubber viscosity is such that it does not flow into the sleeve lumens 86 and 88. The sleeves 82 and 84 are preferably formed of PTFE (polytetrafluoroethylene) or ETFE (ethylene tetra fluoroethylene) or other fluoropolymer (fluorinated ethylene propylene FEP, polyvinylidene fluoride PVDF), HDPE (high density polyethylene), or the like or the like having a low coefficient of friction and are dimensioned to loosely encase the first and second elongated actuator members 52 and 54. The first and second actuator member free ends 62 and 64 are free to move longitudinally within the sleeves 82 and 84 as the distal segment 24 is bent in the first and second directions 42 and 44. In this way, the sleeves 82 and 84 provide slippage between the first and second actuator members 52 and 54 and the catheter body sidewall when the first and second actuator members 52 and 54 are activated and bend or deflect the distal segment 24. The first and second actuator members 52 and 54 and first and second actuator member free ends 62 and 64 are therefore not bound to the distal segment sidewall and are free to move in the first and second directions 42 and 44.

The sleeves 82 and 84 are preferably formed by flattening a thin-wall tube of fluoropolymer and closing its distal end. Although the sleeves 82 and 84 are depicted as the same size in FIG. 4, it will be understood that sleeve 82 can be made smaller in cross-section to accommodate the first elongated actuator member 52.

As can be seen in FIG. 4, the first and second elongated actuator members 52 and 54 are formed of a common SMA layer 66 and a common adhesive layer 68. The traces overlie the adhesive layer as shown in the embodiments of FIGS. 2 and 5.

Figure 5:
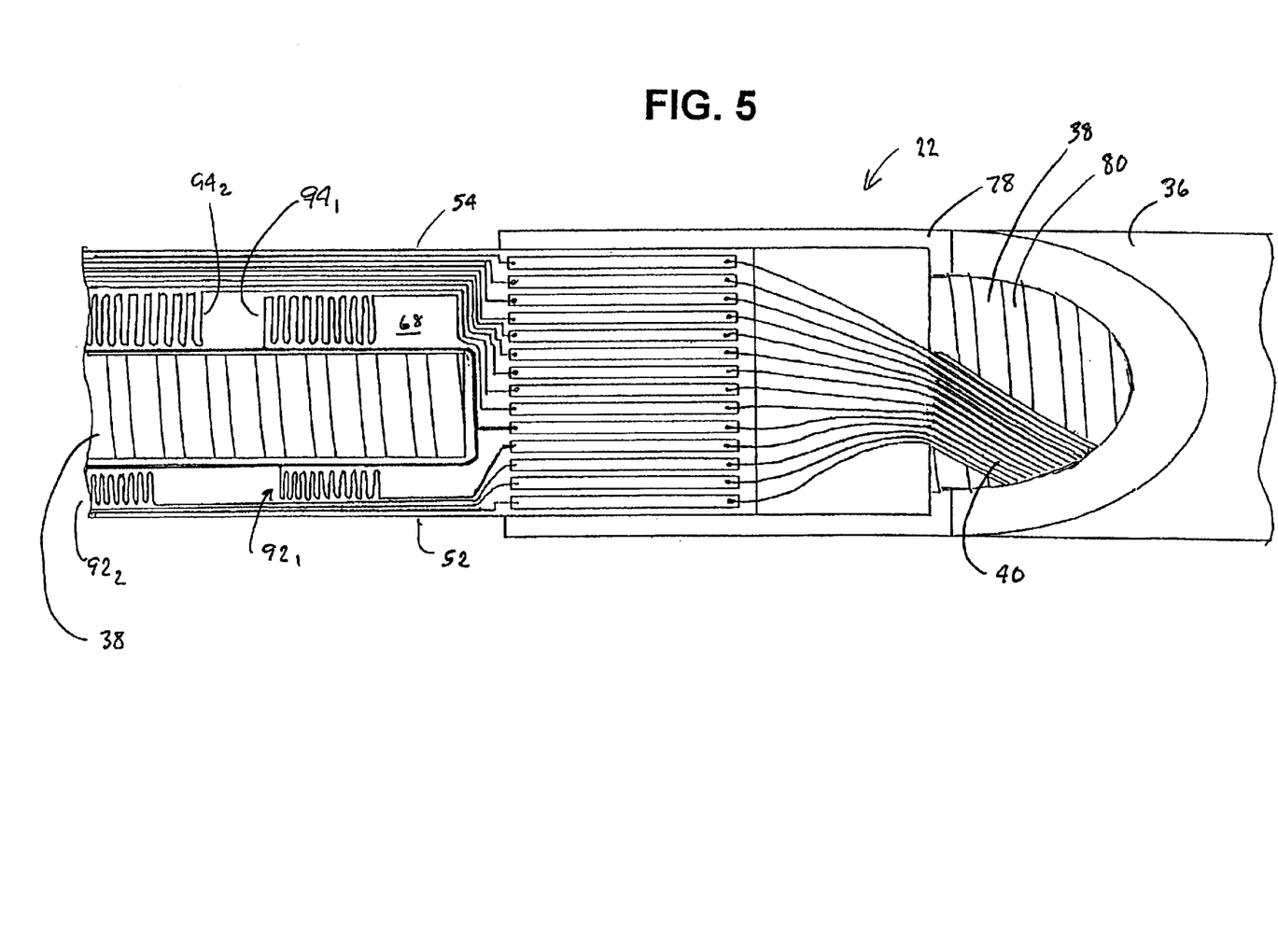
FIG. 5 is an expanded, partial plan view of a proximal portion of the SMA actuator extending distally from the junction of the proximal and distal segments of the catheter body illustrating the preferred ways of forming the distal segment.

The preferred embodiment of the present invention depicted in FIG. 5 employs the indirect heating techniques disclosed in the above-referenced commonly assigned '154 patent wherein a radiant heating element is formed over the adhesive layer 66 employing integrated circuit manufacturing techniques. The radiant heating element heats up when current is delivered through it, and the heat is radiated and conducted through the intervening adhesive layer to the portion of the SMA layer below the radiant heating element, causing a localized bending of the SMA layer when the temperature reaches the transition temperature.

A first plurality of heating elements $92_1$–$92_m$ are formed in a first heating element array along the length of the first elongated actuator member 52, where m=4 in this example. Each heating element $92_1$–$92_m$ is spatially displaced from one another and disposed in operative relation to a respective underlying portion of the SMA layer 66 of the first elongated actuator member 52. The number "m", and the lengths and the widths of the radiant heating elements $92_1$–$92_m$ can be optimized to effect the degree of bending of the distal segment 22 in the first direction 42 that can be achieved. Few heating elements $92_1$–$92_m$ are necessary if the first elongated actuator member 52 is employed simply to straighten the distal segment 24 as described above.

A second plurality of heating elements $94_1$–$94_n$ are formed in a second heating element array along the length of the second elongated actuator member 54, where n=9 in this example. Each heating element $94_1$–$94_n$ is spatially displaced from one another and disposed in operative relation to a respective underlying portion of the SMA layer 66 of the second elongated actuator member 54. The number "n" and the lengths and the widths of the radiant heating elements $94_1$–$94_n$ can be optimized to effect the degree of bending of the distal segment 22 in the second direction 44 that can be achieved. A relatively greater number of heating elements $94_1$–$94_n$ are desirable if the second elongated actuator member 54 is employed to effect U-shaped bends as depicted in FIG. 1 or complex curves in the distal segment 24 as described above.

Thus, second elongated actuator member can advantageously be formed more robustly than the first elongated actuators to operate as a power actuator member that moves or bends the distal segment through a wide range of motion by making it physically larger and having a greater number of heating elements. The first elongated actuator member can advantageously be formed less robustly by making it narrower and with fewer and differently shaped heating elements. In this way, the less robust, first elongated actuator member can be more easily moved or bent by the power actuator member and can be used to simply restore the distal segment into axial alignment with the proximal segment to remove a bend in the distal segment formed by the power actuator member.

The first and second elongated actuator members 52 and 54 of this second embodiment can be fabricated in a variety of ways. For example, a silicon wafer is used as a sacrificial surface in fabrication of the first plurality of heating elements $92_1$–$92_m$ and the second plurality of heating elements $94_1$–$94_n$. A polyimide slurry is spun coated over the surface and polymerized. The serpentine heater traces are deposited onto the polyimide (electrically isolated from the silicon wafer). A second coat of polyimide is spun onto the serpentine heater trace. A mask is placed over the polyimide, and exposed, to light energy, e.g., UV light. The exposed area is polymerized, and the unexposed areas are employed in forming the vias. A chemical is used to remove polyimide from the via area, and the vias are deposited where the unexposed polyimide is removed. The electrical traces and bond pads are then deposited onto the polyimide layer and vias, making electrical continuity from bond pads, through the traces, through the vias, through the heater serpentines, through another set of vias, to the ground traces. A final polyimide layer is spun on for full encapsulation, except for an unexposed area over the bond pads. The unexposed polyimide over the bond pads is then chemically removed. The actuation bond pads are electrically continuous to the ground pad. These heater systems are then attached to the SMA component, using adhesive.

As described above, the second elongated actuator member 54 is more robust than the first actuator member 52 and is used as the primary actuator member to form bends in or deflect the distal segment by a desired amount. The first, less robust, actuator member 52 is relatively easier to deflect so that work performed by the more robust actuator member 54 is lessened. The less robust actuator 52 is activated to move the distal segment back into substantially axial alignment with the proximal segment. The first and second actuator members 54 and 52 extend side-by-side in substantially a common plane and are each configured to move in opposite first and second directions when independently activated. Thus, the first and second actuator members 52 and 54 do not directly bend against one another when activated.

The indirect heating of the SMA actuator members of the second embodiment offers several advantages. The direct electrical connection of wires to convey current for resistance heating creates a "dead zone" where the SMA memory property is destroyed. Secondly, high current, e.g., 0.5–3.0 amp DC, is required for activating a SMA response in a direct resistance heating mode, whereas only 20–50 milliamps DC may be required to indirectly heat an adjacent portion of the SMA layer. Also, achieving a robust electrical connection in a manufacturing setting tends to be difficult for segments that will flex during use. Moreover, the shape of the flexible heating resistance elements is almost unlimited, whereas the direct resistive heating of a SMA layer or element follows the electrical path.

By these examples, it is shown that the present invention provides a manner of optimizing the use of SMA actuator members to form bends or deflect the distal segments of elongated medical instruments. It will be understood that the principles of the present invention can be employed in a wide array of elongated medical instruments of the types described above and that are developed in the future.

Although the examples described above speak of only one bendable distal segment effected through the use of SMA actuator members in an elongated medical instrument, it will be understood that more than one such bendable distal segment can be fabricated along the length of any given instrument body so that more complex bends of multiple distal segments of a medical instrument can be attained. Each such bendable distal segment may be aligned in the same or differing bending planes.

In a further variation of the above-described embodiments, one or more additional elongated actuator member to the first and second elongated actuator members 52, 54 can be formed therewith extending side-by-side in substantially a common plane. For example, a pair of less robust elongated actuator members 52 can be disposed to extend along both sides of the more robust elongated actuator member 54.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of elongated medical instruments that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. An elongated medical instrument configured to be inserted into a body, comprising:

an elongated instrument body having a proximal segment and a distal segment;

a temperature-activated actuator coupled to the distal segment of the elongated instrument body, the actuator comprising first and second elongated actuator members extending side-by-side in substantially a common plane and each configured to move in opposite directions when independently activated;

a first heating device coupled to the first elongated actuator member and configured to deliver thermal energy to the first elongated actuator member to activate the first elongated actuator member and cause the first elongated actuator member to move the distal segment in a first direction;

a second heating device coupled to the second elongated actuator member and configured to deliver thermal energy to the second elongated actuator member to activate the second elongated actuator member and cause the second elongated actuator member to move the distal segment in a second direction opposed to the first direction, wherein the elongated instrument body has an instrument body axis and sidewall extending between an instrument body proximal end and an instrument body distal end, and the temperature-activated actuator is being mounted in the instrument body sidewall such that first and second elongated actuator members extend substantially parallel to the instrument body axis; and means for providing slippage between the first and second actuator members and the instrument body sidewall when the first and second actuator members are activated, wherein the slippage providing means comprises:

first and second elongated sleeves formed in side-by side relation within the sidewall of the distal segment;

the first sleeve formed of a material having a low coefficient of friction and dimensioned to loosely encase the first elongated actuator member, whereby the first elongated actuator member is free to move longitudinally within the sleeve as the distal segment is moved in the first or second direction; and the second sleeve formed of a material having a low coefficient of friction and dimensioned to loosely encase the second elongated actuator member, whereby the first elongated actuator member is free to move longitudinally within the sleeve as the distal segment is moved in the first or second direction.

2. The instrument of claim 1, wherein:

the first and second actuator members are joined together at a fixed actuator end;

the first actuator member extends within the first sleeve distally to a respective first actuator member free end; and the second actuator member extends within the second sleeve distally to a respective second actuator member free end, whereby the first and second actuator member free ends are free to move in the first and second directions.

3. The instrument of claim 2, wherein:

the first elongated actuator member is formed of a layer of shape memory alloy material that retains an elevated temperature shape memory that induces a deflection of the first actuator member free end in the first direction when heated to a transition temperature; and the second elongated actuator member is formed of a layer of shape memory alloy material that retains an elevated temperature shape memory that induces a deflection of the second actuator member free end in the second direction when heated to a transition temperature.

4. The instrument of claim 2, wherein:

the first elongated actuator member comprises a first elongated layer of shape memory alloy material that retains an elevated temperature shape memory effecting movement in the first direction when heated to a transition temperature; and the first heating device comprises:

a first plurality of heating elements in a first heating element array, each heating element spatially displaced from one another and disposed in operative relation to a respective spatially displaced portion of the first layer of shape memory alloy material; and means for selectively energizing one or more of the first plurality of heating elements to selectively heat one or more respective portion of the first layer of shape memory material and induce a deflection of the first actuator member free end in the first direction that is proportional to the number of the heated portions and the spatial relation of the heated portions.

5. The instrument of claim 4, wherein:

the second elongated actuator member comprises a second elongated layer of shape memory alloy material that retains an elevated temperature shape memory effecting movement in the second direction when heated to a transition temperature; and the second heating device comprises:

a second plurality of heating elements in a second heating element array, each heating element spatially displaced from one another and disposed in operative relation to a respective spatially displaced portion of the second layer of shape memory alloy material; and means for selectively energizing one or more of the second plurality of heating elements to selectively heat one or more respective portion of the second layer of shape memory material and induce a deflection of the second actuator member free end in the second direction that is proportional to the number of the heated portions and the spatial relation of the heated portions.

6. The instrument of claim 1, wherein:

the first elongated actuator member is formed of a layer of shape memory alloy material that retains an elevated temperature shape memory that induces a deflection of the first actuator member free end in the first direction when heated to a transition temperature; and the second elongated actuator member is formed of a layer of shape memory alloy material that retains an elevated temperature shape memory that induces a deflection of the second actuator member free end in the second direction when heated to a transition temperature.

7. The instrument of claim 1, wherein:

the first elongated actuator member is formed of a layer of shape memory alloy material that retains an elevated temperature shape memory that induces a deflection of the first actuator member free end in the first direction when heated to a transition temperature; and the second elongated actuator member is formed of a layer of shape memory alloy material that retains an elevated temperature shape memory that induces a deflection of the second actuator member free end in the second direction when heated to a transition temperature.

8. The instrument of claim 1, further comprising means for providing slippage between the first and second actuator members and the instrument body sidewall when the first and second actuator members are activated.

9. The instrument of claim 8, wherein the slippage providing means comprises:

first and second elongated sleeves formed in side-by side relation within the sidewall of the distal segment;

the first sleeve formed of a material having a low coefficient of friction and dimensioned to loosely encase the first elongated actuator member, whereby the first elongated actuator member is free to move longitudinally within the sleeve; and the second sleeve formed of a material having a low coefficient of friction and dimensioned to loosely encase the second elongated actuator member, whereby the first elongated actuator member is free to move longitudinally within the sleeve.

10. The instrument of claim 9, wherein:
the first and second actuator members are joined together at a fixed actuator end;
the first actuator member extends within the first sleeve distally to a respective first actuator member free end; and
the second actuator member extends within the first sleeve distally to a respective first actuator member free end.

11. An elongated medical instrument configured to be inserted into a body, comprising:
an elongated instrument body having an instrument body axis, an instrument body proximal segment, and an instrument body distal segment;
a temperature-activated shape memory alloy actuator coupled to the distal segment of the elongated instrument body, the actuator comprising first and second elongated actuator members extending side-by-side in substantially a common plane in parallel with the instrument body axis to first and second elongated actuator member free ends;
the first elongated actuator member further comprising a first elongated layer of shape memory alloy material that retains an elevated temperature shape memory effecting movement of the first elongated actuator member and the distal segment in a first direction;
a first heating device comprising:
a first plurality of heating elements in a first heating element array, each heating element spatially displaced from one another and disposed in operative relation to a respective spatially displaced portion of the first layer of shape memory alloy material; and
means for selectively energizing one or more of the first plurality of heating elements to selectively heat one or more respective portion of the first layer of shape memory material and induce a deflection of the first actuator member free end in the first direction that is proportional to the number of the heated portions and the spatial relation of the heated portions;
the second elongated actuator member comprises a second elongated layer of shape memory alloy material that retains an elevated temperature shape memory effecting movement in a second direction; and
the second heating device comprises:
a second plurality of heating elements in a second heating element array, each heating element spatially displaced from one another and disposed in operative relation to a respective spatially displaced portion of the second layer of shape memory alloy material; and
means for selectively energizing one or more of the second plurality of heating elements to selectively heat one or more respective portion of the second layer of shape memory material and induce a deflection of the second actuator member free end in the second direction that is proportional to the number of the heated portions and the spatial relation of the heated portions.

12. The instrument of claim 11, wherein:
the elongated instrument body has an instrument body sidewall extending between an instrument body proximal end and an instrument body distal end; and
the temperature-activated actuator is mounted in the instrument body sidewall such that first and second elongated actuator members extend substantially parallel to the instrument body axis.

13. An elongated medical instrument configured to be inserted into a body comprising:
an elongated instrument body having a proximal segment and a distal segment that are aligned axially;
a temperature-activated actuator coupled to the distal segment of the elongated instrument body, the actuator comprising first and second elongated actuator members extending side-by-side in substantially a common plane and each configured to move the distal segment out of axial alignment with the proximal segment when independently activated;
means for delivering thermal energy to the first elongated actuator member to activate the first elongated actuator member and cause the first elongated actuator member to move the distal segment in a first direction out of the common plane;
means for delivering thermal energy to the second elongated actuator member to activate the second elongated actuator member and cause the second elongated actuator member to move the distal segment in a second direction out of the common plane and opposed to the first direction;
first and second elongated sleeves formed in side-by side relation within the sidewall of the distal segment;
the first sleeve formed of a material having a low coefficient of friction and dimensioned to loosely encase the first elongated actuator member, wherein the first elongated actuator member is free to move longitudinally within the sleeve as the distal segment is moved in the first or second direction; and
the second sleeve formed of a material having a low coefficient of friction and dimensioned to loosely encase the second elongated actuator member, wherein the first elongated actuator member is free to move longitudinally within the sleeve as the distal segment is moved in the first or second direction.

14. The instrument of claim 13, wherein the means for delivering thermal energy to the first elongated actuator member comprises means for selectively heating one or more portion of the first elongated actuator member to induce a deflection of the first actuator member in the first direction that is proportional to the number of the heated portions and the spatial relation of the heated portions.

15. The instrument of claim 14, wherein the means for delivering thermal energy to the second elongated actuator member comprises means for selectively heating one or more portion of the second elongated actuator member to induce a deflection of the second actuator member in the second direction that is proportional to the number of the heated portions and the spatial relation of the heated portions.

16. The instrument of claim 13, wherein:
the elongated instrument body has an instrument body axis and sidewall extending between an instrument body proximal end and an instrument body distal end; and
the temperature-activated actuator is mounted in the instrument body sidewall such that first and second elongated actuator members extend substantially parallel to the instrument body axis.

17. An elongated medical instrument to be advanced through the body comprising:
an elongated instrument body having an instrument body extending between an instrument body proximal end and an instrument body distal end and having axially aligned instrument body proximal and distal segments joined at a junction;

the instrument body distal segment further comprising a shape memory alloy actuator supported by said catheter body extending longitudinally from the junction of the instrument body proximal section with the instrument body distal section through at least a portion of said instrument body distal segment;

the shape memory alloy actuator comprising first and second elongated shape memory alloy members extending substantially in parallel with one another;

the first shape memory alloy member is thermally trained to deflect the instrument body distal segment in a first direction when heated by application of energy thereto to a transition temperature;

the second shape memory alloy member is formed to be more robust than the first shape memory alloy member and thermally trained to deflect the instrument body distal segment in a second direction generally opposed to the first direction when heated by application of energy thereto to a transition temperature;

means for selectively conducting energy to at least portions of the second shape memory alloy member to effect selective deflection of the distal segment in the second direction out of axial alignment with the proximal segment and through a relatively wide range of motion; and means for selectively conducting energy to at least portions of the first shape memory alloy member to effect selective deflection of the distal segment in the second direction through a relatively narrow range of motion to substantially restore the axial alignment of the distal segment with the proximal segment, wherein:

the first elongated actuator member comprises a first elongated layer of shape memory alloy material that retains an elevated temperature shape memory effecting movement in the first direction when heated to a transition temperature; and a first heating device comprising:
  a first plurality of heating elements in a first heating element array, each heating element spatially displaced from one another and disposed in operative relation to a respective spatially displaced portion of the first layer of shape memory alloy material; and means for selectively energizing one or more of the first plurality of heating elements to selectively heat one or more respective portion of the first layer of shape memory alloy material and induce a deflection of the first actuator member free end in the first direction that is proportional to the number of the heated portions and the spatial relation of the heated portions.

18. The instrument of claim 17, wherein:

the second elongated actuator member comprises a second elongated layer of shape memory alloy material that retains an elevated temperature shape memory effecting movement in the second direction when heated to a transition temperature; and the second heating device comprises:
  a second plurality of heating elements in a second heating element array, each heating element spatially displaced from one another and disposed in operative relation to a respective spatially displaced portion of the second layer of shape memory alloy material; and means for selectively energizing one or more of the second plurality of heating elements to selectively heat one or more respective portion of the second layer of shape memory material and induce a deflection of the second actuator member free end in the second direction that is proportional to the number of the heated portions and the spatial relation of the heated portions.

19. The elongated medical instrument of claim 17, wherein:

the elongated instrument body has an instrument body axis extending between an instrument body proximal end and an instrument body distal end and sidewall in the instrument body distal segment; and the shape memory alloy actuator is supported by said catheter body sidewall along one side of the catheter body sidewall and extending longitudinally from the junction of the instrument body proximal section with the instrument body distal section through at least a portion of said instrument body distal segment such that first and second elongated actuator members extend substantially parallel to the instrument body axis.

* * * * *